US011617436B1

(12) United States Patent
McNannay et al.

(10) Patent No.: US 11,617,436 B1
(45) Date of Patent: Apr. 4, 2023

(54) SECURE MEDICAL CABINET

(71) Applicant: Curadite, Inc., Beaverton, OR (US)

(72) Inventors: Dennis Michael McNannay, Portland, OR (US); Dewey Nigma, Jr., Beaverton, OR (US)

(73) Assignee: CURADITE, INC., Beaverton, OR (US)

( * ) Notice: Subject to any disclaimer, the term of this patent is extended or adjusted under 35 U.S.C. 154(b) by 492 days.

(21) Appl. No.: 16/827,131

(22) Filed: Mar. 23, 2020

Related U.S. Application Data

(60) Provisional application No. 62/821,610, filed on Mar. 21, 2019.

(51) Int. Cl.
| | |
|---|---|
| *A47B 67/02* | (2006.01) |
| *G16H 40/20* | (2018.01) |
| *G16H 20/13* | (2018.01) |
| *G07C 9/00* | (2020.01) |
| *G06K 7/10* | (2006.01) |
| *A47B 31/00* | (2006.01) |
| *E05G 1/10* | (2006.01) |
| *A61J 1/03* | (2006.01) |
| *A61G 12/00* | (2006.01) |
| *A61J 7/04* | (2006.01) |

(52) U.S. Cl.
CPC .............. *A47B 67/02* (2013.01); *A47B 31/00* (2013.01); *A61G 12/001* (2013.01); *A61J 1/03* (2013.01); *A61J 7/0481* (2013.01); *E05G 1/10* (2013.01); *G06K 7/10297* (2013.01); *G07C 9/00571* (2013.01); *G07C 9/00912* (2013.01); *G16H 20/13* (2018.01); *G16H 40/20* (2018.01); *A47B 2031/006* (2013.01); *A47B 2067/025* (2013.01); *A61J 2200/30* (2013.01); *A61J 2200/70* (2013.01); *A61J 2205/60* (2013.01)

(58) Field of Classification Search
CPC ... A47B 67/02; A47B 31/00; A47B 2067/025; A47B 2031/006; G16H 40/20; G16H 20/13; A61G 12/001; A61J 1/03; A61J 7/0481; A61J 2200/70; A61J 2205/60; A61J 2200/30; E05G 1/10; G06K 17/10297; G07C 9/00571; G07C 9/00912
See application file for complete search history.

(56) References Cited

U.S. PATENT DOCUMENTS

| | | | | |
|---|---|---|---|---|
| 5,728,999 | A * | 3/1998 | Teicher | G07F 11/30 235/380 |
| 6,294,999 | B1 * | 9/2001 | Yarin | G16H 20/13 705/2 |
| 7,258,249 | B1 * | 8/2007 | Frederick | G07F 11/62 312/246 |
| 7,304,582 | B2 * | 12/2007 | Kerr, II | G16H 40/67 700/242 |
| 8,342,400 | B1 * | 1/2013 | Reese | G16H 20/13 340/568.1 |
| 9,934,366 | B1 * | 4/2018 | Zanuzoski | G16H 20/13 |

(Continued)

*Primary Examiner* — Michael Collins
(74) *Attorney, Agent, or Firm* — Alleman Hall Creasman & Tuttle LLP

(57) ABSTRACT

An example medical cabinet system disclosed herein includes a computing system that selectively enables access to a medication pack or other object based on a dispensing schedule, stores event data relating to operation of the cabinet system, and transmits that event data to a remote computing system over a communications network.

17 Claims, 7 Drawing Sheets

(56) References Cited

U.S. PATENT DOCUMENTS

| | | | | |
|---|---|---|---|---|
| 10,346,590 | B2 * | 7/2019 | Coughlin | G07F 11/46 |
| 11,260,524 | B2 * | 3/2022 | Savage | B25H 3/06 |
| 2007/0244598 | A1 * | 10/2007 | Shoenfeld | G16H 20/13 |
| | | | | 700/236 |
| 2012/0130534 | A1 * | 5/2012 | Wurm | G07F 17/0092 |
| | | | | 700/236 |
| 2013/0282392 | A1 * | 10/2013 | Wurm | G06Q 10/087 |
| | | | | 705/2 |
| 2019/0214123 | A1 * | 7/2019 | Parviainen | A47F 3/002 |
| 2020/0005231 | A1 * | 1/2020 | Nakagawa | H04W 4/021 |

* cited by examiner

SECURE MEDICAL CABINET

CROSS REFERENCE TO RELATED APPLICATIONS

This non-provisional application claims priority to U.S. provisional patent application Ser. No. 62/821,610, filed Mar. 21, 2019, titled "SECURE MEDICATION CABINET", the entire contents of which are incorporated herein by reference for all purposes.

BACKGROUND

Access to medications may be closely controlled to conform to a prescribed dispensing schedule. However, adherence to medication storage, access, supervision, and consumption protocols pose significant challenges, both within and outside of an institutional setting.

SUMMARY

An example medical cabinet system disclosed herein includes a computing system that selectively enables access to a medication pack or other object based on a dispensing schedule, stores event data relating to operation of the cabinet system, and transmits that event data to a remote computing system over a communications network.

DETAILED DESCRIPTION

Figure 1A:
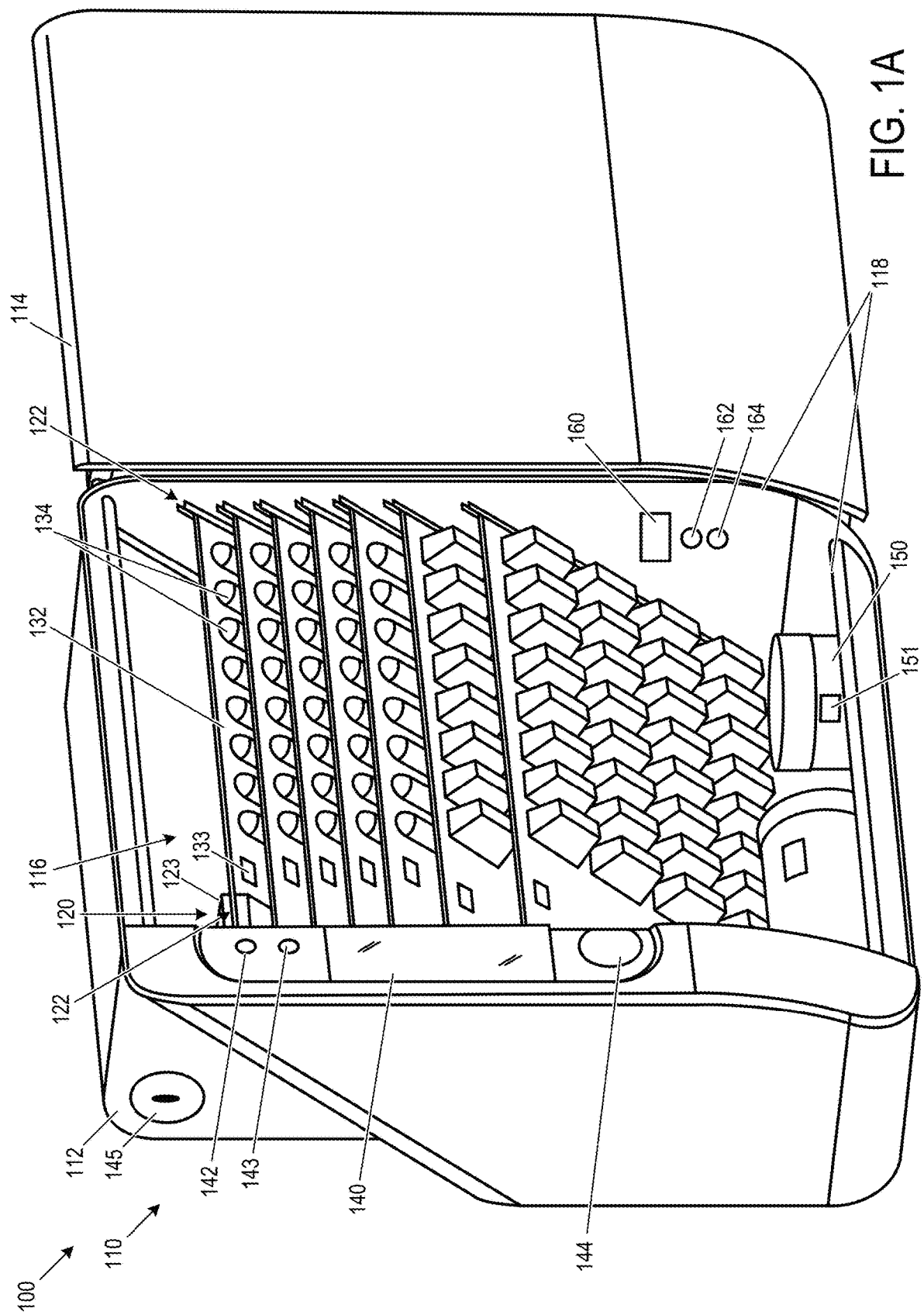
FIGS. 1A and 1B depict an example medical cabinet system.
Figure 1B:
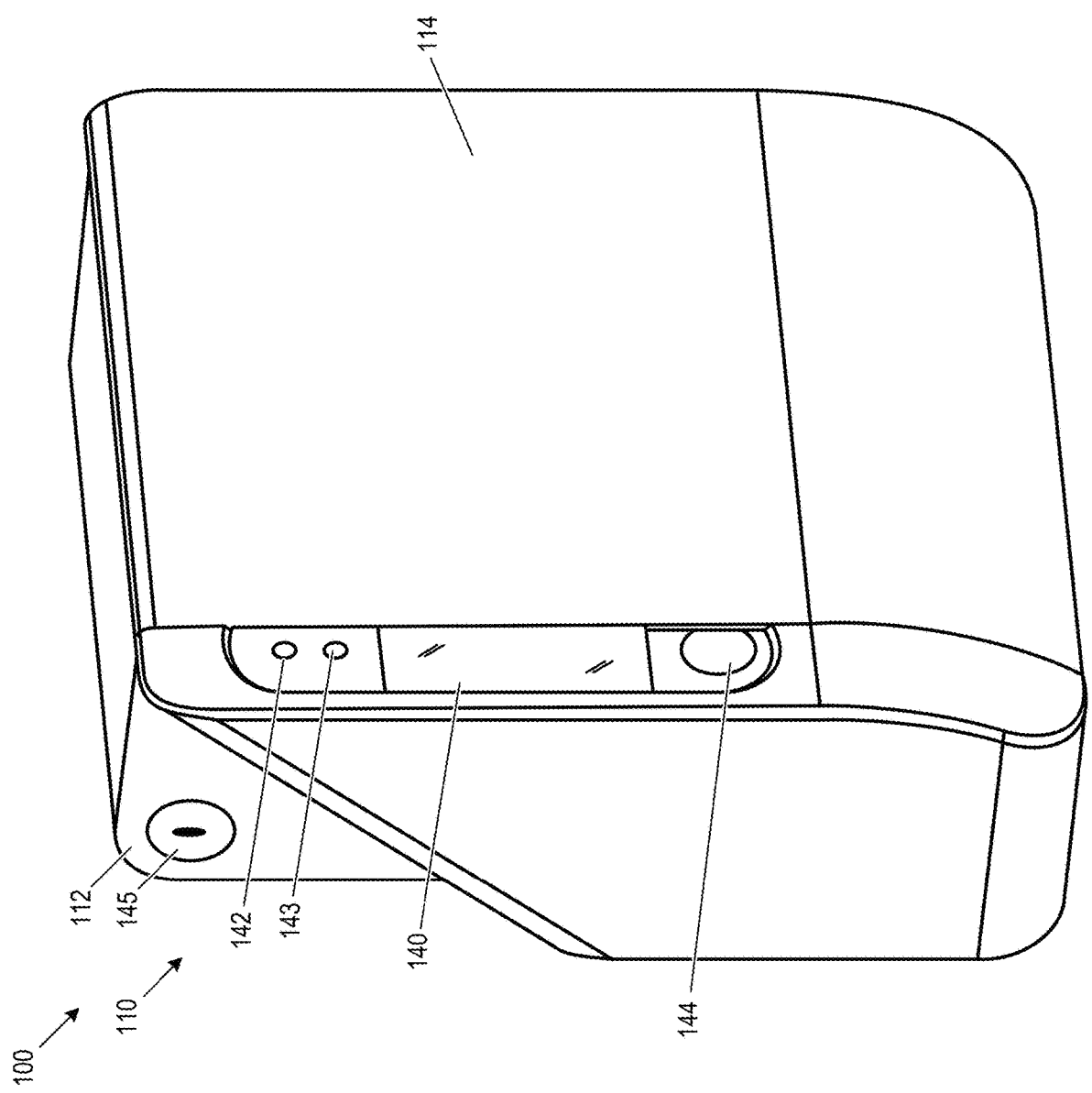

FIGS. 1A and 1B depict an example medical cabinet system 100 in an opened and closed configuration, respectively. Cabinet system 100 includes a cabinet enclosure 110 defined by an enclosure body 112 and an enclosure door 114 collectively forming a storage region 116 therein. Enclosure door 114 is operable to open and close with respect to an opening 118 of enclosure body 112 to selectively enable access to storage region 116. In some examples, cabinet system 100 may provide refrigeration or air conditioning (cooling or heating) to storage region 116 to maintain its contents within a target temperature range. Enclosure body 112 may include a mounting structure that may be used to securely mount the cabinet system to another structure, such as a wall, furniture, vehicle interior, or to another instance of the cabinet system to form a group of cabinets. In some examples, cabinet system 100 can include a set of casters, wheels, rollers, or an intermediate roller cart or stand structure mounted to an underside of enclosure body 112 that enables the cabinet system to be made mobile (e.g., by rolling) within an environment.

Cabinet system 100 may include a door lock assembly that is operable to lock and unlock enclosure door 114, which may be responsive to an electronic command or may be mechanically operated by a user (e.g., via a key and/or handle). In some examples, emergency access to storage region 116 and its contents may be enabled via a handle, lever, or other mechanical feature that unlocks enclosure door 114 and additionally triggers a local alarm (e.g., audible and/or visual) at the cabinet system and/or transmits notification of the emergency access from the cabinet system to a remote device via a communications network. In some examples, cabinet enclosure 110 may include multiple discrete storage regions each with a respective enclosure door that opens and closes independently of the other enclosure doors. In these examples, each enclosure door may have its own respective door lock assembly that is operable to individually lock and unlock that enclosure door. Furthermore, in these examples, each discrete storage region can include respective instances of the various components describe herein with respect to example storage region 116 of FIG. 1.

In some examples, multiple instances of cabinet system 100 may be connected to each other for added storage capacity and/or functionality. A primary cabinet system could provide power and/or bi-directional communications to daisy chained secondary cabinet systems via wired and/or wireless connections. The secondary cabinet system may have a lower cost to manufacture by eliminating the need for instances of the secondary cabinet to have their own respective communications and power modules, while keeping their functionality the same or similar to the primary cabinet system.

Cabinet system 100 may include a storage assembly 120 located within storage region 116 that defines one or more storage receptacles, of which storage receptacle 122 is an example. Storage assembly 120 may be mounted to an interior surface of enclosure body 112, as an example. Each storage receptacle accommodates a respective medication pack or other object, of which medication pack 132 is an example. Each medication pack is storable within and removable from a respective storage receptacle of storage assembly 120. In the example depicted in FIG. 1A, medication pack 132 is stored within receptacle 122 formed by a slot. However, other suitable receptacles may be used depending, for example, on the form factor of the medication pack or object.

Storage assembly 120 may include a receptacle lock assembly 123 for each storage receptacle that is operable to individually lock and unlock a medication pack or other object within that storage receptacle. In example, this receptacle lock assembly can be locked and unlocked responsive to an electronic command or can be mechanically operated by a user (e.g., via a key and/or handle) to lock and unlock the object from the receptacle. In some examples, emergency access to a particular storage receptacle and its contents may be enabled via a handle, lever, or other mechanical feature that unlocks the storage receptacle and additionally triggers a local alarm (e.g., audible and/or visual) at the cabinet system and/or transmits notification (e.g., as event data) of the emergency access from the cabinet system to a remote device via a communications network.

A medication pack or other object may include one or more discrete medication enclosures. As an example, medication pack 132 may take the form of a blister pack that includes multiple discrete medication enclosures 134. However, other suitable medication pack or object form factors may be used. Furthermore, the example medication packs described herein may instead refer to other types of objects that include medications, diagnostics, wound dressings, ointments, syringes, equipment, materials, devices, or other suitable objects for which access is to be controlled. These objects may include containers having one or more discrete enclosures for holding contents.

Cabinet system 100 may be used to store other objects in addition to or in the alternative to medication packs. For example, digital diagnostic devices such as a temperature sensing device, blood pressure sensing device, lab-on-a-chip device, MEMS device, etc. may be secured within storage region 116. In some examples, storage assembly 120 may include receptacles that accommodate digital diagnostic devices or other objects, and a receptacle lock assembly may be provided to individually lock and unlock these objects within their respective storage receptacles, such as discussed above with respect to the medication packs. Furthermore, at least some objects may be stored within cabinet system 100 without being specifically assigned to a receptacle. For example, an example object 150 is depicted within storage region 116 resting on a floor surface of the enclosure. Object 150 may take the form of a medication container containing one or more doses of medication or another type of object for which access is to be controlled.

Each medication pack (e.g., 132) or other object (e.g., 150) can each include one or more identifier components by which an identifier of that medication pack or object can be read by the cabinet system or other device. For example, medication pack 132 includes an identifier component 133, and object 150 includes an identifier component 151. In an example, identifier components include a wireless interface having a wireless receiver, transmitter, and/or transceiver (e.g., NFC, Bluetooth, etc.) that communicates (e.g., transmits) wireless signals indicating an identifier (e.g., an RFID identifier or other suitable identifier type) of the identifier component, and therefore identifies the object to which the identifier component is attached or associated. In some examples, the identifier component can additionally wirelessly receive (e.g., harvest) energy from a wireless interface of the cabinet system and/or report additional information (e.g., a state of medication enclosures 134) to a wireless interface of the cabinet system.

Cabinet system 100 can include one or more wireless interfaces having a wireless receiver, transmitter, and/or transceiver indicated schematically at 160 that communicates (e.g., receives) wireless signals and/or energy to or from identifier components (e.g., 133 and 151). Wireless signals received from identifier components can include the identifier of the identifier component of the medication pack or object, and may additionally include a state of one or more enclosures (e.g., 134) of the medication pack or object.

In at least some examples, the wireless interfaces of the cabinet system can be tuned or beamformed to the storage region of the cabinet system to increase wireless signal strength within the storage region and to reduce wireless signal strength for areas located outside of the enclosure and storage region of the cabinet. This tuning or beamforming of wireless signals can be used to distinguish wireless signals originating from within the storage region from wireless signals originating from outside of the enclosure and storage region based on wireless signal strength. Thus, wireless signal strength can be used to determine whether an object is located within the storage region or outside of the storage region.

Additionally or alternatively, identifier components include an optical code (e.g., a bar code, QR code, etc.) that can be optically scanned or otherwise read by an optical sensor of the cabinet system or other device. Cabinet system 100 can include one or more optical sensors indicated schematically at 162 that images optical codes from identifier components (e.g., 133 and 151). Optical sensor 162 in this example images an interior of storage region 116. However, optical sensors may be additionally or alternatively located on an exterior of cabinet system 100. Cabinet system 100 can include one or more light sources indicated schematically at 164 that can be used alone or in combination with optical sensors (e.g., 162) to project light into an interior of storage region 116. For example, light source 164 can be used to optically scan optical codes of identifier components (e.g., 133 and 151). As another example, light source 164 can illuminate storage region 116 and its contents with light (e.g., ultraviolet light) under select conditions (e.g., after door 114 is closed and/or locked) to sterilize or disinfect the objects stored within the storage region from bacteria, viruses, organisms, or other contaminants. As another example, light (e.g., visible light) projected by light sources can be used to illuminate the interior of storage region 116 while the door is opened to enable a user to locate objects within the storage region. Light projected by light sources (e.g., 164) can include one or more of ultraviolet, visible, near-ultraviolet wavelengths, or other suitable wavelengths depending on implementation.

In some examples, enclosure body 112 and enclosure door 114 of cabinet system 100 can include, incorporate, and/or be formed by materials (e.g., metals) and/or material configurations (e.g., Faraday cage mesh, films, layers, etc.) that provide electromagnetic shielding between storage region 116 and an exterior of the cabinet system. This shielding can be used by the cabinet system to distinguish, based on signal strength, wireless signals communicated with wireless interfaces of objects located within storage region 116 from wireless signals communicated with wireless interfaces of objects located outside of the cabinet system (particularly when enclosure door 114 is closed). For example, while enclosure door 114 is closed, wireless signals communicated by wireless interfaces 133, 151, etc. located within storage region 116 to the cabinet system via wireless interface 160 can be distinguished from wireless signals transmitted from external sources based on the wireless signal strength (e.g., exceeding a threshold strength).

In some examples, a digital scale may be provided within storage region 116 or on an external surface of cabinet system 100 that enables objects (e.g., medications) to be weighed and their weight values recorded, stored, and reported off-board the cabinet system. A plurality of digital scales may be associated with some or all of the receptacles to provide verification that objects have been returned to their receptacles and/or specified amounts of medication have been dispensed.

Cabinet system 100 may include one or more user interfaces, such as a graphical display 140 (e.g., touch-sensitive or traditional), optical sensor 142 (e.g., a camera), RFID/NFC scanner 143, biometric input device 144 (e.g., optical sensor for fingerprint or eye scanning, or microphone), mechanical lock interface 145 with keyhole, buttons, indicator lights, digital scales, etc. Cabinet system 100 may further include an on-board computing system, sensor subsystem, communications subsystem, refrigeration and/or air conditioning subsystem, and power subsystem, among other components not depicted in FIGS. 1A and 1B. Additional aspects of a cabinet system 100 will be described in further detail with reference to FIG. 2.

Figure 2:
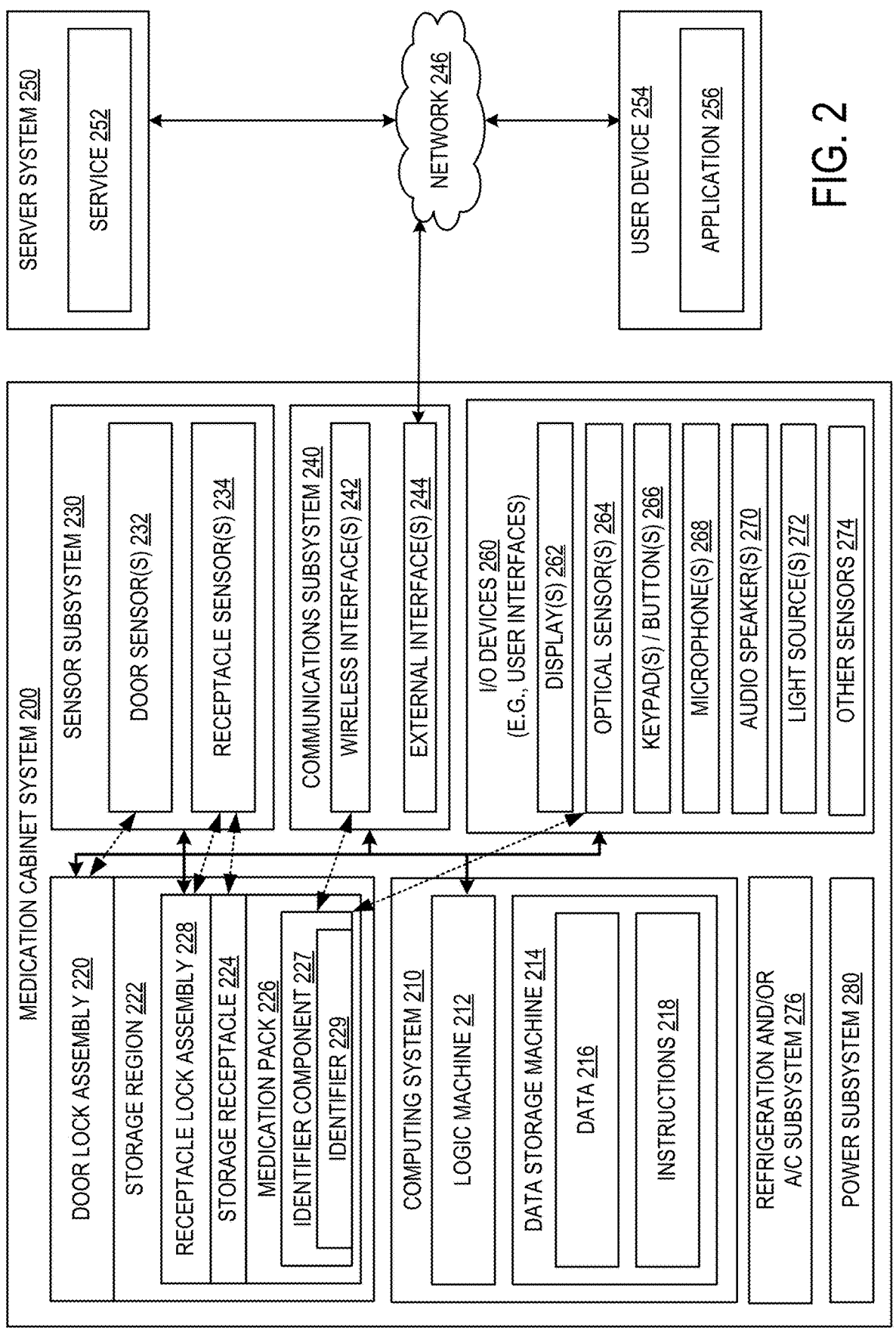
FIG. 2 is a schematic diagram depicting an example medical cabinet system describing additional aspects of the medical cabinet system of FIGS. 1A and 1B.

FIG. 2 is a schematic diagram depicting an example medical cabinet system 200 of which medical cabinet system 100 of FIGS. 1A and 1B is an example. Cabinet system 200 includes a computing system 210, including a logic machine 212 and a data storage machine 214 having data 216 and/or executable instructions 218 stored thereon. Instructions 218 may be executed by logic machine 212 to implement or perform any of the methods or operations described herein. Aspects of computing system 210 are described in further detail with reference to example computing system 700 of FIG. 7. Any of the data measured or conditions determined by computing system 210 of the cabinet system can be stored at data storage machine 214 as data 216.

As previously described with reference to FIGS. 1A and 1B, a cabinet system may include a door lock assembly 220 associated with an enclosure door of a storage region 222 of the cabinet system. Door lock assembly 220 may be operable to lock and unlock its enclosure door responsive to an electronic command initiated by computing system 210. Door lock assembly 220 may be omitted from cabinet system 200 in some examples.

Within storage region 222, a storage receptacle 224 of cabinet system 200 accommodates a removable medication pack 226. However, it will be understood that medication pack 226 may instead refer to any other object (e.g., object 150 of FIG. 1) to be secured within cabinet system 200, such as a digital diagnostics device. As previously described with reference to FIG. 1A, each medication pack or object can include an identifier component having a respective identifier. FIG. 2 depicts an example of medication pack 226 including an identifier component 227 having an identifier 229. Identifier component 227 can include a wireless transceiver or transmitter, and/or an optical code, as examples. Identifier 229 can be read from identifier component 227 by the one or more wireless interfaces 242 and/or one or more optical sensors 264 of cabinet system 200. In other examples, the one or more wireless interfaces 242 can be replaced with or augmented by a physical electronic connector of the cabinet system that is configured to mate with a corresponding electronic connector of identifier component 227 of each medication pack or object.

Cabinet system 200 further includes a receptacle lock assembly 228 associated with storage receptacle 224. Receptacle lock assembly 228 may be operable to lock the medication pack within the storage receptacle in which the medication pack is not removable from the storage receptacle, and unlock the medication pack from the storage receptacle in which the medication pack is removable from the storage receptacle. In some example, storage receptacles and/or receptacle lock assemblies may be omitted from cabinet system 200.

The various lock assemblies disclosed herein with respect to door lock assembly 220 and receptacle lock assembly 228 may include electro-mechanical and/or electro-magnetic components that are controlled by computing system 210 to engage or disengage a physical locking mechanism responsive to electronic commands (e.g., signals) output by computing system 210. As an example, a latch forming a post, shaft, or other suitable element may be extended from a first feature through a portion of a second feature (e.g., a latch receptacle) to be locked to the first feature, and may be retracted from the second feature to unlock the second feature from the first feature. For example, a post may be extended from a surface of a storage receptacle through an opening or notch formed in a medication pack to retain the medication pack within the storage receptacle. In another example, door lock assembly 220 includes a first component that is mounted to or forms part of the enclosure door and a second component that is mounted to or forms part of the enclosure body (e.g., the door frame), and an electromagnetic or electromechanical actuator that interfaces with the first or second component is operable to lock or unlock the door responsive to an electronic command. For example, the first component of the door lock assembly may take the form of a latch or a latch receptacle, and the second component of the door lock assembly may take the form of the other of the latch or the latch receptacle. As another example, the first component of the door lock assembly may take the form of an electromagnet or a magnetically attractive element (e.g., a permanent magnet or a ferromagnetic material), and the second component may take the form of the other of the electromagnet or the magnetically attractive element. However, other suitable door lock configurations may be used for the door lock assembly. The door lock assembly 220 and/or the receptacle lock assembly 228 may be manually locked and unlocked via a physical key.

Cabinet system 200 includes a sensor subsystem 230 having one or more sensors. For example, sensor subsystem 230 may include one or more door sensors 232 associated with the enclosure door and/or its door lock assembly 220. The one or more door sensors 232 may be operable to detect a door state for the enclosure door of the cabinet assembly as being locked or unlocked by the door lock assembly. Alternatively or additionally, the one or more door sensors 232 may be operable to detect a door state for the enclosure door of the cabinet assembly as being open or closed. Door sensors 232 can use optical, magnetic, electromagnetic, or electronic interaction between a sensor or component of the enclosure door, enclosure body, lock assembly and another sensor or component of the enclosure door, enclosure body, lock assembly to detect the door state. Examples include Hall effect sensors, stepper motor position sensors (e.g., of an electromechanical lock), optical sensing, mating of electronic connectors to establish an electric signal across the mated connectors, etc.

Sensor subsystem 230 may include one or more receptacle sensors 234 associated with each storage receptacle (e.g., storage receptacle 224) and/or its receptacle lock assembly (e.g., receptacle lock assembly 228) of the cabinet system. The one or more receptacle sensors 234 may be operable to detect a receptacle state for storage receptacle 224 as being locked or unlocked by the receptacle lock assembly. Alternatively or additionally, the one or more receptacle sensors 234 may be operable to detect whether medication pack 226 is present within storage receptacle 224 via optical, magnetic, electromagnetic, or electronic interaction between a sensor or component of the storage receptacle and a sensor or component of the medication pack or other object that can be accommodated by the receptacle. Examples include Hall effect sensors, stepper motor position sensors (e.g., of an electromechanical lock), optical sensing, mating of electronic connectors to establish an electric signal across the mated connectors, etc.

Cabinet system 200 includes a communications subsystem 240 having one or more communications interfaces. Any of the data measured or conditions determined by computing system 210 of the cabinet system can be transmitted to another computing device or computing system via communications subsystem 240 as will be described in further detail with reference to the event data of FIG. 4. As an example, communications subsystem 240 may include one or more wireless interfaces 242 each having a wireless receiver, transmitter, or transceiver for personal area network wireless communications, local area network wireless communications, and/or wide-area network wireless communications supporting NFC communications, Bluetooth, Wi-Fi, or other suitable wireless protocol. The one or more wireless interfaces 242 may be used to detect presence of medication pack 226 within storage region 222 and/or within storage receptacle 224. In an example, a near-field wireless receiver (e.g., reader) of the one or more wireless interfaces 242 is located within storage region 222 of the cabinet system to detect transmission of wireless communications from a near-field wireless transmitter (e.g., tag) of medication pack 226. When medication pack 226 is removed from storage receptacle 224 and/or from storage region 222, a signal strength between medication pack 226 and the one or more wireless interfaces 242 may drop below a threshold, thereby indicating that medication pack 226 is not present within storage region 222 and/or its receptacle 224. In some examples, medication pack 226 may not include an on-board energy storage device, and may collect and utilize energy received from NFC wireless transmissions by the one or more wireless interfaces 242. For example, medication pack 226 may utilize passive RFID technologies. In addition or as an alternative to detecting presence of medication pack 226, the one or more wireless interfaces 242 may be used to receive a pack identifier from medication pack 226 and/or other data, thereby enabling the medication pack to be identified, distinguished, and usage monitored separate from other medication packs or objects.

While a medication pack may have a variety of form factors, as an example, a medication pack includes: a tray having one or more depressions formed therein with respect to an interior-facing surface of the tray, a backing film interfacing with the interior-facing surface of the tray and enclosing the one or more depressions to form one or more discrete medication enclosures in which the backing film includes a set of electrically conductive traces spanning each of the one or more depressions, a tray-based logic machine interfacing with the set of traces that is programmed with instructions to monitor the enclosure state of each of the one or more discrete medication enclosures via the set of traces, a wireless transmitter, receiver, or transceiver (e.g., NFC, Bluetooth, etc.) interfacing with the tray-based logic machine to transmit data indicating the enclosure state of each of the one or more discrete medication enclosures and an identifier of the medication pack for reception by a wireless receiver of the cabinet system.

Communications subsystem 240 may include one or more external communications interfaces 244 having a receiver and/or transmitter (e.g., transceiver) that supports wired and/or wireless communications over a wide-area network, local-area network, and/or personal-area network, which are depicted in FIG. 2 collectively as network 246. Such communications may support any suitable communications protocol or set of protocols, including cellular, Wi-Fi, Bluetooth, RFID/NFC, IP/TCP, telephony/VoIP technology, etc. In an example, one or more external communications interfaces 244 of communications subsystem 240 may be used by computing system 210 to communicate with a remote computing system over a wide-area network, such as the Internet and/or intermediate wireless cellular and/or local-area networks. Communications subsystem may be operated as a communications hub that enables axillary or peripheral devices to communicate with each other or with a remote computing system via one or more communications networks. Examples of a remote computing system include a server system 250 (e.g., a cloud server platform) hosting a service 252, and a user device 254 executing an application program 256. Service 252 may take the form of a medication tracking and adherence service, as an example. Application program 256 may be specifically configured for interaction with medical cabinet system 200 and/or service 252, and may be used to control features of medical cabinet system 200 or service 252 and/or display data provided by the medical cabinet system or the service. In some example, external communications interfaces 244 can support telephony/VoIP with one or more remotely located user devices to support one-to-one or conference calls between medical personnel, caretakers, patients, etc. using the cabinet system's input/output devices.

Cabinet system 200 includes one or more input/output devices 260 (e.g., user interfaces), such as one or more graphical displays 262 (e.g., a touch-sensitive display or non-touch sensitive display, of which graphical display 140 of FIG. 1 is an example), one or more optical sensors 264 (e.g., a camera or other optical sensor device, of which optical sensors 142, 144, and 162 are examples), one or more keypads/buttons 266, one or more microphones 268 (of which sensor 144 is an example), one or more audio speakers 270, one or more light sources 272 (of which light source 164 of FIG. 1 is an example), one or more other sensors 274, etc. Graphical display 262 may take the form of an integrated display screen, a peripheral display screen, and/or one or more indicator lights having assigned functions. The one or more other sensors 274 can include sensors that provide internal environmental monitoring of the storage region and/or external environmental monitoring of an environment surrounding the cabinet system, including temperature, light, shock/vibration, $CO_2$, etc. Cold storage of pharmaceuticals, for example, may require monitoring of the internal and external temperatures. Other monitoring capabilities may assist with theft/tamper detection, such as shock/vibration monitoring, as an example.

Cabinet system 200 includes a refrigeration and/or air conditioning (A/C) subsystem 276. A/C may include cooling and/or heating of the storage region(s) of the cabinet system. Subsystem 276 may include components suitable for refrigeration and/or A/C functions, including pumps, compressors, valves, working fluid, and associated fluid pathways for circulating the working fluid. The enclosure and/or door of cabinet system 200 may include or provide insulation in at least some examples.

Cabinet system 200 includes a power subsystem 280, which may include a power interface to connect the cabinet system to an electrical outlet and/or an on-board battery or other energy storage device for powering the various components of the medical cabinet system. In some examples, power subsystem 280 may include charging ports and/or wireless charging pads for supplying power to objects (e.g., electronic devices) stored within a storage region of cabinet system and/or objects located external the cabinet system (e.g., additional cabinet system modules). In some examples, power subsystem 280 may be configured to harvest power from wirelessly transmitted power sources.

Figure 3:
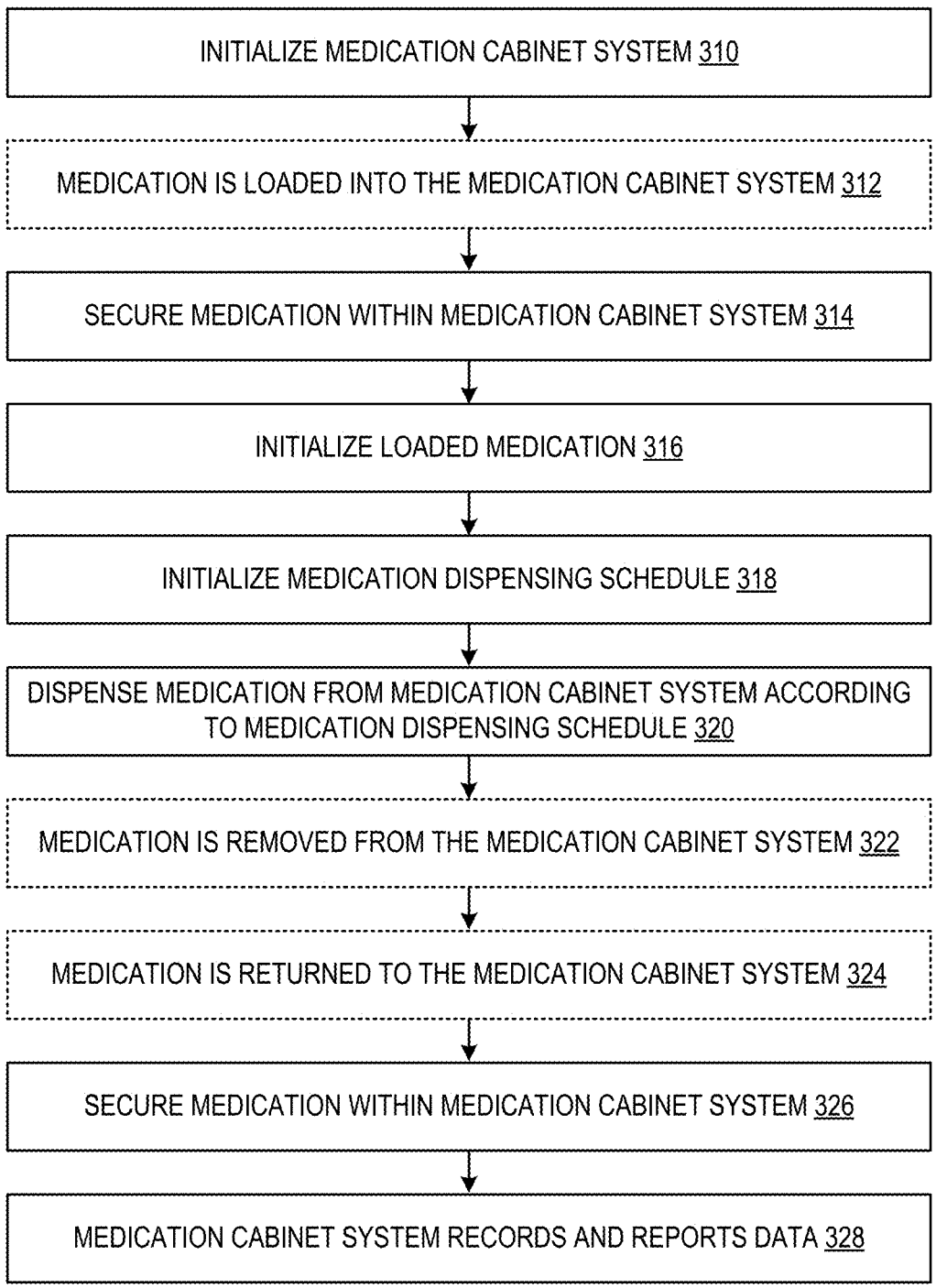
FIG. 3 is a flow diagram depicting an example method that may be performed with respect to the example medical cabinet systems of FIGS. 1 and 2.

FIG. 3 is a flow diagram depicting an example method 300 that may be performed with respect to a medical cabinet system, such as previously described with reference to the example medical cabinet systems of FIGS. 1A, 1B, and 2. Aspects of method 300 may be performed by a computing system, with the exception of operations 312, 322, and 324 indicated by broken lines in FIG. 3 which may be performed manually by a human user. This computing system may reside on-board the medical cabinet system (e.g., computing system 210), off-board the medical cabinet system (e.g., server system 250 and/or user device 254), or may be distributed between on-board computing systems of the medical cabinet system and one or more other off-board computing systems or computing devices. Operations of method 300 briefly introduced with reference to FIG. 3 will be described in further detail with reference to example method 400 of FIG. 4.

At 310, the medical cabinet system is initialized. Initialization may include communications between a computing system of the cabinet system (e.g., computing system 210) and a remote computing system, such as server system 250 and/or user device 254 of FIG. 2. As an example, a user may login to the cabinet system to assign access control privileges, unlock an enclosure door and/or a storage receptacle, request download of a medication dispensing schedule, associate human patients with the cabinet system, etc. In some examples, unlock commands may be initiated from a remote computing system, such as a server or a user device.

At 312, medication is loaded into the medical cabinet system by a user. For example, one or more medication packs may be loaded into a storage region and/or into one or more storage receptacles of the medical cabinet. While the methods described herein refer to medication and/or medication packs stored within the cabinet system, it will be understood that these methods may be applied to other types of objects, such as medication containers, digital diagnostics devices, or other objects described herein for which access control is to be provided.

At 314, the medication is secured within the medical cabinet system. For example, an enclosure door may be closed and locked, and/or storage receptacles may be locked to retain medication packs therein. In some examples, lock commands may be initiated from a remote computing system, such as a server or a user device.

At 316, the medication loaded into the medical cabinet system is initialized. The cabinet system may detect identifiers of the respective medication packs or other objects loaded into the cabinet system, and may store and communicate those identifiers to a remote computing system, such as a server system hosting a service or a user device. Detection of identifiers may be performed wirelessly via the one or more wireless interfaces 242 and/or optically via one or more optical sensors 264 reading an identifier component (e.g., 227) associated with the medication pack or other object.

At 318, a medication dispensing schedule is initialized with respect to the medication loaded into the medical cabinet. For example, for each medication pack and each human patient associated with the cabinet system, a medication dispensing schedule for that medication/patient pair may be requested and/or pushed by a remote computing system (e.g., hosting a service or an application program) to the computing system on-board the cabinet system, which is then stored on-board the cabinet system.

At 320, medication is dispensed from the medical cabinet system according to the medication dispensing schedule. For example, the enclosure door and/or storage receptacle corresponding to an appropriate medication pack may be unlocked to enable the medication pack to be removed from the cabinet system. User interfaces (e.g., display, audio speaker, etc.) of the cabinet system may output an indication that a particular medication is ready to be dispensed to a particular patient, or such indication may be output via an application program of a user device (e.g., application program 256). Additionally, an indication a quantity of medication and/or an enclosure door/storage receptacle may be output by the cabinet system or an application program of a user device.

At 322, medication is removed from the medical cabinet system by a user. For example, a user may remove a medication pack containing the medication to enable the medication to be dispensed to a patient. In some example, data relating to the dispensing of the medication may be captured by the cabinet system via a user interface, such as a camera and/or microphone to confirm that the medication was dispensed and consumed by the patient. Such data may be stored and/or transmitted off-board the cabinet system to another computing system.

At 324, medication is returned to the medical cabinet system by a user. For example, a user may place the medication pack containing a remainder of the medication (if any) within the storage region and/or storage receptacle of the cabinet system from which the individual medication pack was removed.

At 326, the medication is secured within the medical cabinet system. For example, an enclosure door may be closed and locked, and/or storage receptacles may be locked to retain medication packs therein. In some examples, one or more light sources located within the storage region (e.g., 116) of the storage cabinet may be operated for a period of time after the enclosure door is closed and/or locked to emit ultraviolet light to sterilize or disinfect objects and surfaces within the storage region.

At 328, the medical cabinet system records and reports data captured before, during, and/or after dispensing medication or other objects from the cabinet system. Such data may be stored locally in a data storage machine and/or may be transmitted to a remote computing system, such as server system 250 and/or user device 254 of FIG. 2 as event data. In at least some examples, operation 328 may be performed responsive to a command received from a remote computing device or system, such as a user device or server system. Furthermore, in at least some examples, data recorded at operation 328 may trigger the computing system of the cabinet to perform additional tasks. As an example, the cabinet system may query a user to provide a current count of medication packs, medication doses, or other objects within the storage region via a user interface of the cabinet system or a user device connected via a network. This count may serve as a ground truth for the recalibration of quantities or identities of objects within the storage region.

Figure 4:
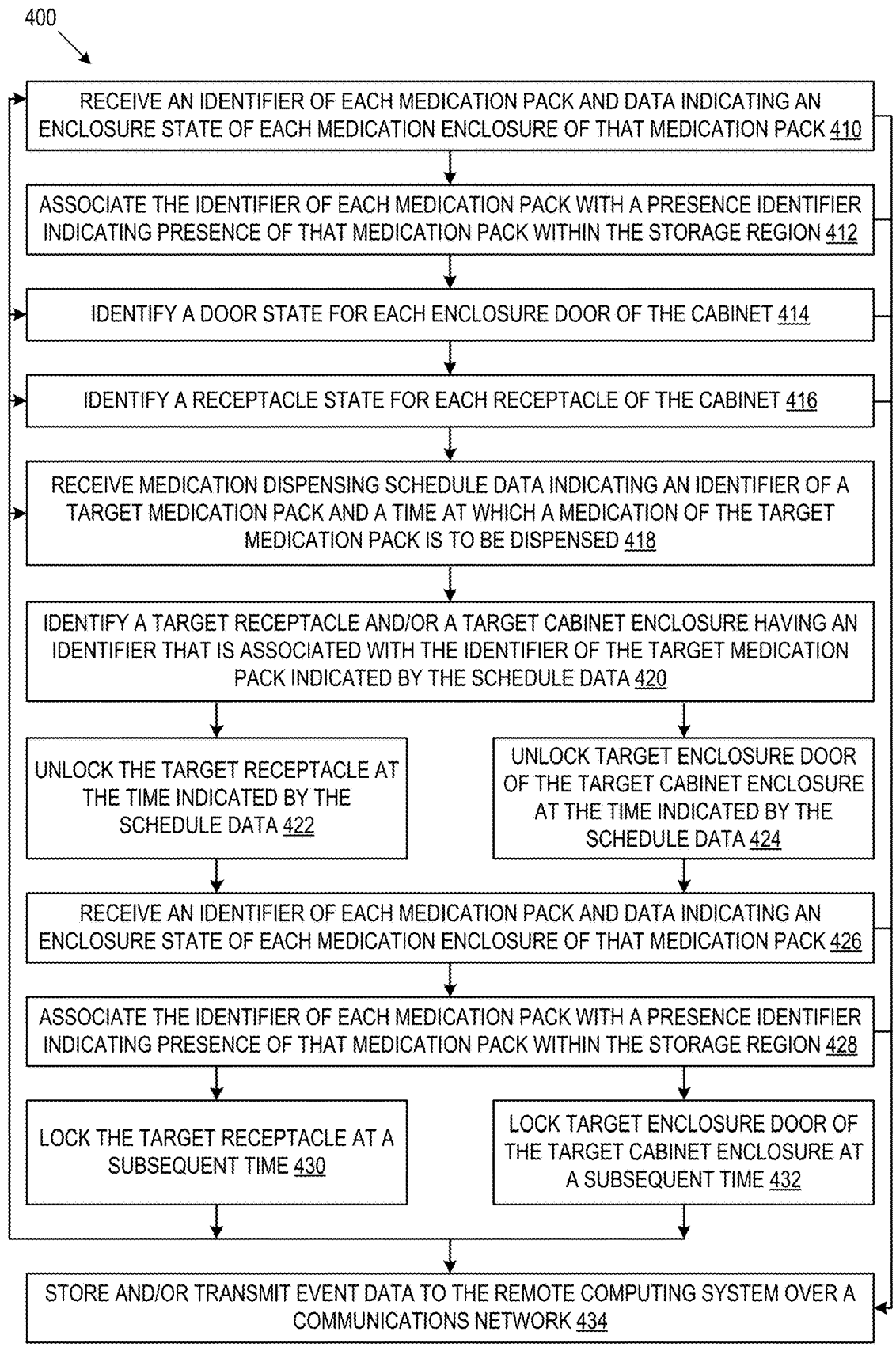
FIG. 4 is a flow diagram depicting an example method describing additional aspects of the method of FIG. 3.

FIG. 4 is a flow diagram depicting an example method 400 that may be performed with respect to a medical cabinet system, such as previously described with reference to FIGS. 1A, 1B, and 2. Aspects of method 400 may be performed by a computing system, such as previously described with reference to method 300 of FIG. 3. Furthermore, while the methods described herein refer to medication and/or medication packs stored within the cabinet system, it will be understood that these methods may be applied to other types of objects, such as medication containers, digital diagnostics devices, or other objects described herein for which access control is to be provided.

At 410, an identifier of each medication pack and data indicating an enclosure state of each medication enclosure of that medication pack are received. For example, operation 410 may be performed repeatedly (e.g., at a predefined frequency) until all medication packs are confirmed as being returned to and present within their target enclosures and/or target receptacles or for a predefined duration. The identifier of each medication pack and its data may be received or otherwise read via one or more wireless interfaces 242 and/or one or more optical sensors 264, as examples. As an example, an object is determined to be located within the storage region when the enclosure door is closed based on a wireless signal strength of wireless signals received from the wireless transmitter of the object exceeding a threshold signal strength. If the signal strength is less than a threshold signal strength when the door is closed, the object can be determined to not be presented within the storage region of the cabinet. As another example, a physical electronic connector may be used to connect logic elements of the medication pack or object (e.g., a monitored device), with a computing system of the cabinet system. For example, each receptacle can include a physical electronic connector that mates with a corresponding electronic connector of the medication pack or object. As yet another example, the identifier and/or data may be manually entered by a user (e.g., via an application running on a separate device or via an input device of the cabinet system).

At 412, the identifier of each medication pack is associated with a presence identifier indicating presence of that medication pack within the storage region of the cabinet system. In some examples, each medication pack that is not confirmed to be present within its respective storage region and/or storage receptacle may be associated with a presence identifier indicating absence of that medication pack. Accordingly, presence of each medication pack may be identified via a wireless interface and/or optical sensor of the cabinet system in at least some examples.

At 414, a door state is identified for each enclosure door of the cabinet system. For example, the door state may be identified via one or more door sensors 232. For example, the door state is identified at 414 as being either locked or unlocked. Alternatively or additionally, the door state is identified as being either opened or closed.

At 416, a receptacle state is identified for each storage receptacle of the cabinet system. For example, the receptacle state may be identified via the one or more receptacle sensors 234 as being either locked or unlocked. Alternatively or additionally, the receptacle state is identified as being either loaded or unloaded with a medication pack or object.

Event data representing any of the identifiers and/or states obtained by operations 410-416 may be stored in a local data storage machine of the cabinet system and/or may be transmitted offboard the cabinet system to a remote computing system over a communications network at 434 and validate authenticity.

At 418, medication dispensing schedule data is received, which indicates an identifier of a target medication pack and a time at which a medication of the target medication pack is to be dispensed. The schedule data may be received over a communications network from a remote computing system (e.g., server system 250 and/or user device 254). In an example, the schedule data may uniquely identify a particular medication pack stored within the cabinet system. However, in some examples, the identifier indicated by the schedule data may identify a class of medication of which multiple medication packs stored within the cabinet system may contain medication that is within that class of medication, in addition to or as an alternative to identifying a particular medication pack. The schedule data may additionally indicate a patient identifier, a caretaker identifier for a person (if any or if different from the patient) that is provided access control privileges with respect to the dispensing of the medication, and a quantity of units of medication to be dispensed at a particular time. The schedule data may indicate multiple dispensing events for a particular medication of a particular quantity and a particular patient that occur over a period of time for each of a plurality of patients and medications. In some examples, schedule data may be provided to the cabinet system at a predefined frequency, may be provided responsive to a request by the cabinet system, and/or may be pushed to the cabinet system responsive to an update to the existing schedule data.

At 420, a target storage receptacle and/or a target cabinet enclosure are identified as having an identifier that is associated with an identifier of the target medication pack indicated by the medication dispensing schedule data. For storage receptacle-level granularity, a separate wireless receiver and/or physical electronic connector may be provided for each storage receptacle to enable a direct association between a particular storage receptacle and a particular medication pack within the cabinet system.

At 422, the target storage receptacle is unlocked at the time indicated by the medication dispensing schedule data. Additionally or alternatively depending on implementation, at 424, the target enclosure door of the target cabinet enclosure is unlocked at the time indicated by the medication dispensing schedule data. In some examples, the target storage receptacle and/or the target enclosure door may remain locked, but may be unlocked responsive to a request from an authorized user (e.g., patient or caretaker) if the current time of the request is within the time indicated by the medication dispensing schedule data. Access to medication may be selectively provided by the cabinet system using a login process, biometric sensing via a user interface (e.g., camera, microphone, etc.), and/or physical proximity of a user device to the cabinet system as detected over a wireless communications network. Biometric sensing may include fingerprint scanning, iris scanning, facial recognition, or voice recognition, as examples.

At 426, an identifier for each medication pack or object and data indicating an enclosure state of each medication enclosure of that medication pack or object are received, as previously described at 410. Again, operation 426 may be performed repeatedly (e.g., at a predefined frequency) until all medication packs or objects are confirmed as being returned to their target enclosures and/or target receptacles or for a predefined duration.

At 428, the identifier or each medication pack is associated with a presence identifier indicating presence of that medication pack within the storage region of the cabinet system. Again, in some examples, each medication pack that is not confirmed to be present within its respective storage region and/or storage receptacle may be associated with a presence identifier indicating absence of that medication pack.

Event data representing any of the identifiers obtained by operations 426 and 428 may be stored in a local data storage machine of the cabinet system and/or may be transmitted offboard the cabinet system to a remote computing system over a communications network at 434. Event data may be programmatically transmitted at 434 offboard the cabinet system to a remote computing system at predetermined intervals and/or responsive to predefined events, such as following dispensing of medication or objects from the cabinet after the cabinet door has been closed or after a threshold period of time following opening of the door or a predefined dispensing time. The event data can include a time stamp for each data item indicating a time at which the data item was detected or captured. As examples, event data may be reported by the cabinet system to a remote computing system in the case where a medication pack is not returned to the cabinet system within a threshold period of time following removal of the medication pack; if an incorrect amount of medication was removed from or is present within the medication pack following return of the medication pack to the cabinet system; or if the medication pack was not removed from the cabinet system within a threshold period following a dispensing time indicated by the dispensing schedule. As another example, if a medication pack or other object to be dispensed was not removed from the storage region, the event data can indicate (e.g., via an identifier) that the medication pack or object was not removed. As another example, if a medication pack or other container was removed, but contents (e.g., medication or object) of that medication pack or container to be dispensed were not removed from the pack or container, the event data can indicate (e.g., via an identifier) that the contents were not removed. As another example, if a medication pack or other object to be dispensed has not been returned to the storage region, the event data can indicate (e.g., via an identifier) that the medication pack or object was not returned to the storage region.

At 430, the target storage receptacle is locked at a subsequent time, such as upon confirming presence of the medication pack within the target storage receptacle. Additionally or alternatively depending on implementation, at 432, the target enclosure door of the target cabinet enclosure is locked at a subsequent time, such as upon confirming presence of the medication pack within its target cabinet enclosure and/or within its target storage receptacle.

Following locking operations performed at operations 420 and/or 432, method 400 may proceed to operation 434 (e.g., to store and/or transmit event data) and/or may return to any of the preceding operations, such as operations 410, 414, 416, and/or 418.

Below, two examples of a sensor-enabled medication package are described. A sensor-enabled medication package can be used by the cabinet system to determine whether medication or another object has been removed from the medication package. The example of FIG. 5 includes an array of sensors embedded in a packaging lid while the example of FIG. 6 uses wireless sensors attached to the same lid structure. Each package may include a unique packaging identifier, a packaging communication module docking base (PCMDB), and a data processing/communication module.

Figure 5:
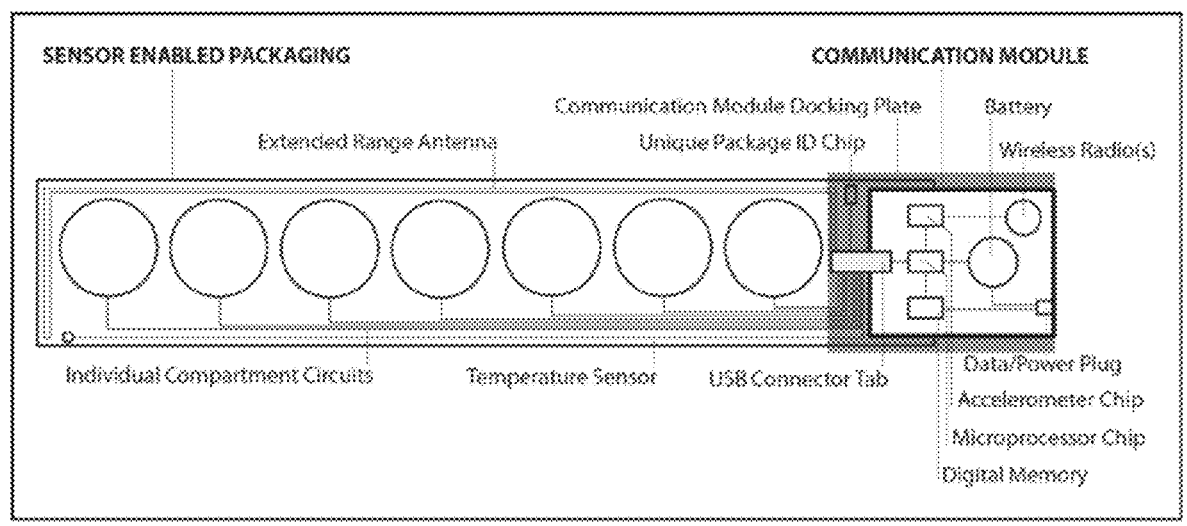
FIGS. 5 and 6 depict examples of sensor-based packaging.
Figure 6:
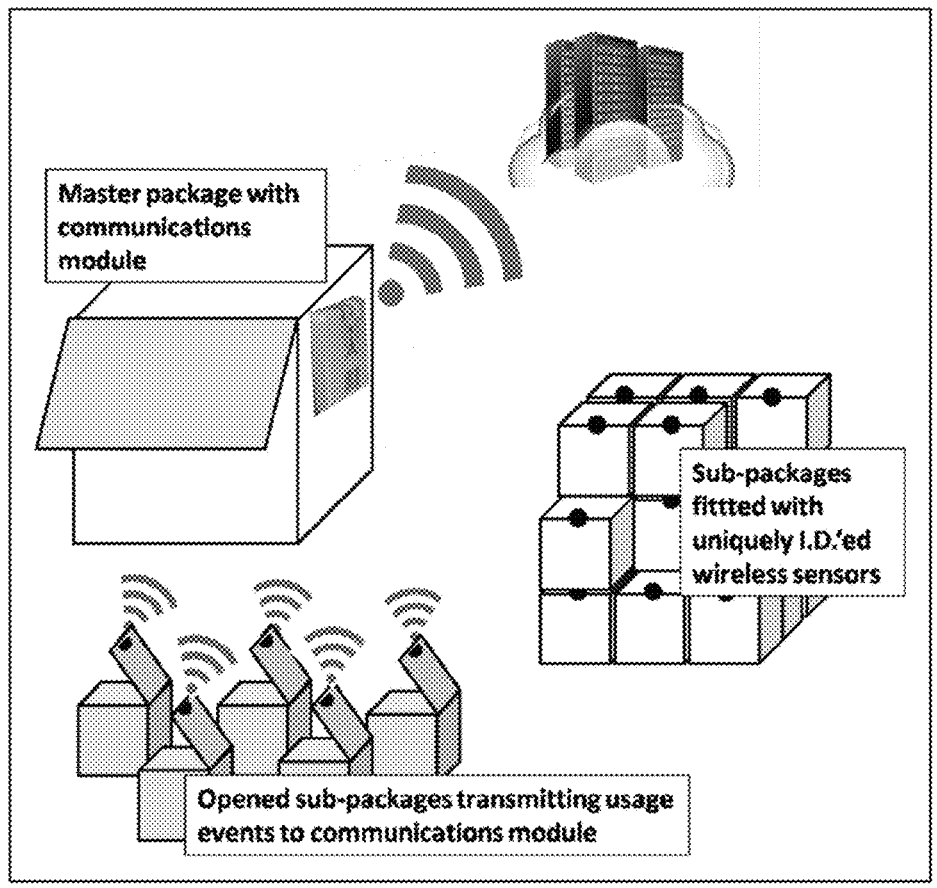

FIG. 5 illustrates a circuit-based embodiment with an array of compartment sensors that are affixed to a lid or cover with a pre-designated set of compartment openings. These sensors are linked to a sensor-enabled lid (manufactured with sensor-enabled openings), which is attached to the matching packaging receptacles consisting of compartments of known dimensions (e.g. a tray of extruded plastic wells) once the package has been provisioned. After being provisioned with contents, the sensor-enabled lid is adhered with pre-applied adhesive or other mechanism, to the container body.

Once provisioned with contents (e.g. specific medications) and sealed with the sensor-enabled lid, the distribution authority (whoever is taking responsibility for managing the package's contents and distribution), may register the package electronically by using the package's embedded identifier to launch a software application. The software application includes an interface to populate the unique digital manifest that was created and stored for future use when the lid was manufactured. As discussed later, the distribution authority will use a software program or interface to complete the packaging process by completing the digital manifest to include the recipient's profile, contents of each compartment, reminder and escalation rules, trusted contacts and digital modes of communication, trusted third-parties, privacy provisions, etc. Once the sensor-enabled lid is permanently sealed onto the package, the uniquely identifiable ID is assigned, and the digital manifest is completed, the sensor-enabled package is considered provisioned.

In another example, a sensor-enabled package could utilize an array of wireless sensors (illustrated in FIG. 6) rather than a circuit-based lid shown in FIG. 5. In this example, wireless sensors are attached to separately packaged (disconnected from each other) sub-packages/compartments. Instead of sensors bonded to the openings of a package's lid to be placed on pre-configured packaging trays/compartments, wireless sensors would be separately attached to individual sub-packages which would then be wirelessly linked to the unique packaging identifier embedded in the PCMDB, which would serve to identify the overall package's identity. Once the primary packaging is opened, the PCMDB, together with its attached communication module, monitor for signals from the array of wireless sensors to determine and monitor the status of each sub-compartment. Similar to the previous embodiment, the usage rules stored in the digital manifest would be applied as the wireless usage events are detected and forwarded to the server through the communication module to the manifest repository.

The packaging may be designed to support multiple form factors, including for example, at the center of a circularly-arranged blister pack, such as the type commonly used for hormone therapy (e.g. the 28-day blister pack used for birth control pills). It may be built into the cap of a medical ointment to verify the usage of the ointment and may have a method to determine the amount of ointment used. Each day/week/time-of-day may have a different marking to provide indications of when the particular drug would be taken. Research studies show that different form factors lead to different compliance rates. Any packaging solution that has ability to detect when a medication was accessed is within the scope and spirit of the invention.

As discussed above, sensor-enabled packaging may rely on a set of compartment sensor(s) that monitor the status of specific package compartments or sub-packages. The individual compartment sensors can be connected to the processor module via a variety of techniques, which could include, but are not be limited to, physical electrical circuits linking each individual packaging compartment to the processor module and communication module. In an example, the circuits in the lid would also link a pre-printed circuitry lining adhered to the lower part of the package's individual compartments. By linking the circuitry in the compartments to the circuitry in the sensor-enabled lid, the communication module would be able to monitor the entire sealed compartment and thus deliver even more rigorous content security. Another method of monitoring could include using individual wireless sensors capable of sending a signal when triggered to the processing module using a wireless signal. In this example the wireless sensors would be capable of harvesting energy from the environment or human touch to perform their sensing function. As an example, a radioactive source with a short half-life could be used for the energy source and also to provide timing. If the particles are alpha particles, they wouldn't pass through the plastic and if the half-life is short, then timing to an accuracy of tens of minutes could be achieved by detecting the rate of emitted particles.

The lid, or associated sensor enabled packaging, may have several different methods of communication and storage, depending on the use case. In one embodiment, a simple lid monitors physical circuits that allow the communication module, when inserted into the PCMDB, to detect all aspects of opening events and identify the PCMDB's unique digital identifier. That is the lid only provides an electrical contact that allows the external device to sense if/when a compartment is opened. External devices (e.g. digital scale, blood pressure cuffs, etc.), including and working in tandem with the communication module, could provide additional processing and/or functions, which might include providing power, date/time, manifest read/write/storage, event recording (including environmental conditions), rules engine updates, and implementation of rules.

In some embodiments, the methods and operations described herein may be tied to a computing system of one or more computing devices. In particular, such methods and operations may be implemented as a computer-application program or service, an application-programming interface (API), a library, and/or other computer-program product.

Figure 7:
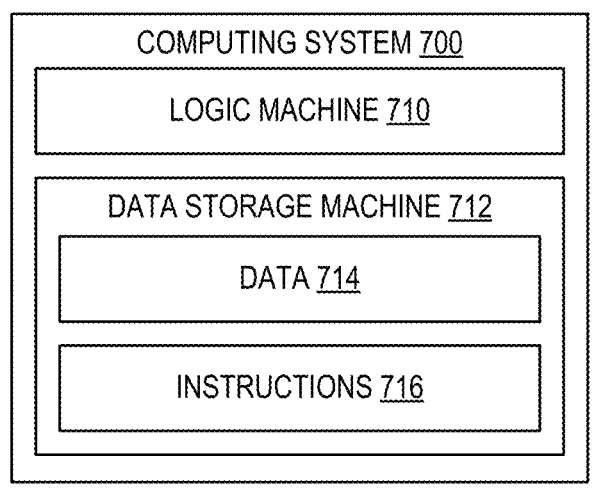
FIG. 7 is a schematic diagram depicting an example computing system.

FIG. 7 schematically shows an example computing system 700 that can enact one or more of the methods and operations described above. Computing system 700 is shown in simplified form, and may represent any of the computing systems or devices described herein. Computing system 700 may take the form of one or more personal computers, server computers, tablet computers, medical cabinet systems, network computing devices, mobile computing devices, and/or other computing devices.

Computing system 700 includes a logic machine 710 and a storage machine 712. Computing system 700 may optionally include other components not shown in FIG. 7, such as those previously described with reference to FIG. 2, for example.

Logic machine 710 includes one or more physical devices configured to execute instructions, such as instructions 716 represented schematically in FIG. 7. For example, the logic machine may be configured to execute instructions that are part of one or more applications, services, programs, routines, libraries, objects, components, data structures, or other logical constructs. Such instructions may be implemented to perform a task, implement a data type, transform the state of one or more components, achieve a technical effect, or otherwise arrive at a desired result.

The logic machine may include one or more processors configured to execute software instructions. Additionally or alternatively, the logic machine may include one or more hardware or firmware logic machines configured to execute hardware or firmware instructions. Processors of the logic machine may be single-core or multi-core, and the instructions executed thereon may be configured for sequential, parallel, and/or distributed processing. Individual components of the logic machine optionally may be distributed among two or more separate devices, which may be remotely located and/or configured for coordinated processing. Aspects of the logic machine may be virtualized and executed by remotely accessible, networked computing devices configured in a cloud-computing configuration.

Storage machine 712 includes one or more physical devices configured to hold data 714 and/or instructions 716 executable by the logic machine to implement the methods and operations described herein. When such methods and operations are implemented, the state of storage machine 712 may be transformed—e.g., to hold different data.

Storage machine 712 may include removable and/or built-in devices. Storage machine 712 may include optical memory (e.g., CD, DVD, HD-DVD, Blu-Ray Disc, etc.), semiconductor memory (e.g., RAM, EPROM, EEPROM, etc.), and/or magnetic memory (e.g., hard-disk drive, floppy-disk drive, tape drive, MRAM, etc.), among others. Storage machine 712 may include volatile, nonvolatile, dynamic, static, read/write, read-only, random-access, sequential-access, location-addressable, file-addressable, and/or content-addressable devices.

It will be appreciated that storage machine 712 includes one or more physical devices. However, aspects of the instructions described herein alternatively may be propagated by a communication medium (e.g., an electromagnetic signal, an optical signal, etc.) that is not held by a physical device for a finite duration.

Aspects of logic machine 710 and storage machine 712 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 700 implemented to perform a particular function. In some cases, a module, program, or engine may be instantiated via logic machine 710 executing instructions 716 held by storage machine 712. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

It will be appreciated that a "service", as used herein, is an application program executable across multiple user sessions. A service may be available to one or more system components, programs, and/or other services. In some implementations, a service may run on one or more server-computing devices.

When included, a display subsystem may be used to present a visual representation of data held by storage machine 712. This visual representation may take the form of a graphical user interface (GUI). As the herein described methods and processes change the data held by the storage machine, and thus transform the state of the storage machine, the state of the display subsystem may likewise be transformed to visually represent changes in the underlying data. A display subsystem may include one or more display devices utilizing virtually any type of technology. Such display devices may be combined with logic machine 710 and/or storage machine 712 in a shared enclosure, or such display devices may be peripheral display devices.

When included, an input subsystem may comprise or interface with one or more user interface devices such as a keyboard, mouse, touch screen, or game controller. In some embodiments, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition.

When included, a communication subsystem may be configured to communicatively couple computing system 700 with one or more other computing devices. Communication subsystem 700 may include wired and/or wireless communication devices compatible with one or more different communication protocols. As non-limiting examples, the communication subsystem may be configured for communication via a wireless telephone network, or a wired or wireless local- or wide-area network. In some embodiments, the communication subsystem may allow computing system 700 to send and/or receive messages to and/or from other devices via a network such as the Internet.

According to an example of the present disclosure, a medical cabinet system comprises: a cabinet enclosure defined by an enclosure body and an enclosure door collectively forming a storage region therein, the enclosure door operable to close and open an opening of the enclosure body to provide access to the storage region; a door lock assembly operable to lock and unlock the enclosure door responsive to an electronic command; a sensor subsystem operable to detect a door state for the enclosure door of the cabinet assembly as being either locked or unlocked, or either opened or closed; a wireless receiver located within the storage region of the cabinet; a communications subsystem to communicate with a remote computing system over a wide-area communications network; a cabinet-based computing subsystem including a cabinet-based data storage machine and a cabinet-based logic machine interfacing with the sensor subsystem, the near-wireless receiver, and the communications subsystem, the cabinet-based logic machine programmed with instructions executable to: receive, via the wireless receiver from a wireless transmitter of an object located within the storage region, an identifier of the object, associate the identifier of the object received via the wireless receiver with a presence identifier indicating presence of the object within the storage region, identify the door state of the enclosure door of the cabinet enclosure, and transmit event data to the remote computing system over the wide-area communications network, the event data indicating the identifier of the object, the door state of the enclosure door, and the presence identifier of the object. In an example, the medical cabinet system can further comprise: a storage assembly located within the storage region of the cabinet enclosure and defining a receptacle that accommodates the object that is removable from the receptacle; and a receptacle lock assembly operable to lock the object within the receptacle in which the object is not removable from the receptacle if the receptacle lock assembly is locked and unlock the object in which the object is removable from the receptacle; the sensor subsystem being further operable to detect a receptacle state for the receptacle as being locked or unlocked by the receptacle lock assembly; and wherein the instructions are further executable by the cabinet-based logic machine to transmit the event data to the remote computing system further indicating the receptacle state. In an example, the object is a medication pack having one or more discrete medication enclosures; and the cabinet-based logic machine is programmed with instructions to: receive, via the wireless receiver from the wireless transmitter of the medication pack located within the storage region, data indicating an enclosure state of one or more medication enclosures of the medication pack, wherein the event data further indicates the enclosure state of each of the one or more medication enclosures of the medication pack. In an example, the logic machine is further programmed with instructions to: receive a medication dispensing schedule data over the wide-area communications network via the communications subsystem, the schedule data indicating an identifier of a target of a set of multiple medication packs and a time at which a medication of the target medication pack is to be dispensed, identify a target cabinet enclosure having an identifier that is associated with the identifier of the target medication pack indicated by the schedule data, and provide an electronic command to the lock assembly to individually unlock the enclosure door of the target cabinet enclosure from an initial locked state at the time indicated by the schedule data. In an example, the cabinet-based logic machine is further programmed with instructions to: at a subsequent time following the time indicated by the schedule data, for at least the target cabinet enclosure: receive the identifier of the target medication pack and the data indicating an updated enclosure state of each of the one or more medication enclosures of the target medication pack via the near-field wireless receiver associated with the target cabinet enclosure, associate the identifier of that target medication pack with the identifier of the target cabinet enclosure within the cabinet-based data storage machine based on the near-field wireless receiver via which the identifier of the target medication pack was received, upon receiving the identifier of the target medication pack, provide a subsequent electronic command to the lock assembly to individually lock the enclosure door of the target cabinet enclosure from an unlocked state at the subsequent time, identify the door state of the enclosure door of the target cabinet enclosure following the subsequent electronic command, and transmit updated event data to the remote computing system over the wide-area communications network, the updated event data indicating the identifier of the target medication pack associated with the identifier of the target cabinet enclosure, the updated enclosure state of each of the one or more medication enclosures of the target medication pack, and the door state of the target enclosure door. In an example, the wireless receiver is a near-field wireless receiver located within the storage region of the cabinet; wherein the cabinet enclosure defined by an enclosure body and an enclosure door provides electromagnetic shielding; and wherein the cabinet-based logic machine is further programmed with instructions to: determine that the object is located within the storage region when the enclosure door is closed based on a wireless signal strength of wireless signals received from the wireless transmitter of the object exceeding a threshold signal strength, the identifier of the object received via the wireless receiver is associated with the presence identifier if the object is determined to be located within the storage region based on the wireless signal strength. In an example, the medical cabinet system further comprises a light source that is operable to illuminate the storage region with ultraviolet light; and the cabinet-based logic machine is further programmed with instructions to operate the light source during a time when the enclosure door is determined to be closed or locked.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A medical cabinet system, comprising:
a cabinet enclosure defined by an enclosure body and an enclosure door collectively forming a storage region therein, the enclosure door operable to close and open an opening of the enclosure body to provide access to the storage region;
a door lock assembly operable to lock and unlock the enclosure door responsive to an electronic command;
a sensor subsystem operable to detect a door state for the enclosure door of the cabinet assembly as being either locked or unlocked, or either opened or closed;
a wireless receiver located within the storage region of the cabinet;
a communications subsystem to communicate with a remote computing system over a wide-area communications network;
a cabinet-based computing subsystem including a cabinet-based data storage machine and a cabinet-based logic machine interfacing with the sensor subsystem, the wireless receiver, and the communications subsystem, the cabinet-based logic machine programmed with instructions executable to:
receive, via the wireless receiver from a wireless transmitter of a medication pack located within the storage region, an identifier of the medication pack, wherein the medication pack has one or more discrete medication enclosures,
associate the identifier of the medication pack received via the wireless receiver with a presence identifier indicating presence of the medication pack within the storage region,
receive, via the wireless receiver from the wireless transmitter of the medication pack located within the storage region, data indicating an enclosure state of each of the one or more medication enclosures of the medication pack,
identify the door state of the enclosure door of the cabinet enclosure, and
transmit event data to the remote computing system over the wide-area communications network, the event data indicating the identifier of the medication pack, the enclosure state of each of the one or more medication enclosures of the medication pack, the door state of the enclosure door, and the presence identifier of the medication pack.

2. The medical cabinet system of claim 1, further comprising:
a storage assembly located within the storage region of the cabinet enclosure and defining a receptacle that accommodates the medication pack that is removable from the receptacle; and
a receptacle lock assembly operable to lock the medication pack within the receptacle in which the medication pack is not removable from the receptacle if the receptacle lock assembly is locked and unlock the medication pack in which the medication pack is removable from the receptacle;
the sensor subsystem being further operable to detect a receptacle state for the receptacle as being locked or unlocked by the receptacle lock assembly; and
wherein the instructions are further executable by the cabinet-based logic machine to transmit the event data to the remote computing system further indicating the receptacle state.

3. The medical cabinet system of claim 1, wherein the medication pack is one of a set of multiple medication packs;
wherein the logic machine is further programmed with instructions to:
receive a medication dispensing schedule data over the wide-area communications network via the communications subsystem, the schedule data indicating an identifier of a target medication pack of the set of multiple medication packs and a time at which a medication of the target medication pack is to be dispensed,
identify a target cabinet enclosure having an identifier that is associated with the identifier of the target medication pack indicated by the schedule data, and
provide an electronic command to the lock assembly to individually unlock the enclosure door of the target cabinet enclosure from an initial locked state at the time indicated by the schedule data.

4. The medical cabinet system of claim 3, wherein the cabinet-based logic machine is further programmed with instructions to:
at a subsequent time following the time indicated by the schedule data, for at least the target cabinet enclosure:
receive the identifier of the target medication pack and the data indicating an updated enclosure state of each of the one or more medication enclosures of the target medication pack via the wireless receiver associated with the target cabinet enclosure,
associate the identifier of that target medication pack with the identifier of the target cabinet enclosure within the cabinet-based data storage machine based on the wireless receiver via which the identifier of the target medication pack was received,
upon receiving the identifier of the target medication pack, provide a subsequent electronic command to the lock assembly to individually lock the enclosure door of the target cabinet enclosure from an unlocked state at the subsequent time,
identify the door state of the enclosure door of the target cabinet enclosure following the subsequent electronic command, and
transmit updated event data to the remote computing system over the wide-area communications network, the updated event data indicating the identifier of the target medication pack associated with the identifier of the target cabinet enclosure, the updated enclosure state of each of the one or more medication enclosures of the target medication pack, and the door state of the target enclosure door.

5. The medical cabinet system of claim 1, wherein the wireless receiver is a near-field wireless receiver located within the storage region of the cabinet;
wherein the cabinet enclosure defined by an enclosure body and an enclosure door provides electromagnetic shielding; and
wherein the cabinet-based logic machine is further programmed with instructions to:
determine that the medication pack is located within the storage region when the enclosure door is closed based on a wireless signal strength of wireless signals received from the wireless transmitter of the medication pack exceeding a threshold signal strength,
wherein the identifier of the medication pack received via the near-field wireless receiver is associated with the presence identifier if the medication pack is determined to be located within the storage region based on the wireless signal strength.

6. The medical cabinet system of claim 1, wherein the medical cabinet system further comprises a set of wheels, rollers, or casters.

7. A method performed by a computing system with respect to a medical cabinet system, the method comprising:
at a cabinet enclosure of the medical cabinet system defined by an enclosure body and an enclosure door collectively forming a storage region therein:
receiving, via a wireless receiver from a wireless transmitter of a medication pack located within the storage region, an identifier of the medication pack, wherein the medication pack has one or more discrete medication enclosures;
associating the identifier of the medication pack received via the wireless receiver with a presence identifier indicating presence of the medication pack within the storage region;
receiving, via the wireless receiver from the wireless transmitter of the medication pack located within the storage region, data indicating an enclosure state of each of the one or more discrete medication enclosures of the medication pack;
identifying, via a sensor subsystem, a door state of the enclosure door of the cabinet enclosure as being either locked or unlocked, or either opened or closed; and
transmitting, via a communications subsystem, event data to a remote computing system over a wide-area communications network, the event data indicating the identifier of the medication pack, the door state of the enclosure door, the enclosure state of each of the one or more discrete medication enclosures of the medication pack, and the presence identifier of the medication pack.

8. The method of claim 7, wherein the medical cabinet system further includes:
a storage assembly located within the storage region of the cabinet enclosure that defines a receptacle that accommodates the medication pack that is removable from the receptacle, and
a receptacle lock assembly operable to lock the medication pack within the receptacle in which the medication pack is not removable from the receptacle if the receptacle lock assembly is locked and unlock the medication pack in which the medication pack is removable from the receptacle,
wherein the sensor subsystem being further operable to detect a receptacle state for the receptacle as being locked or unlocked by the receptacle lock assembly; and
wherein the method further comprises transmitting the event data to the remote computing system further indicating the receptacle state.

9. The method of claim 7, wherein the medical cabinet system further includes a door lock assembly operable to lock and unlock the enclosure door responsive to an electronic command;
wherein the medication pack is one of a set of multiple medication packs; and
wherein the method further comprises:
receiving a medication dispensing schedule data over the wide-area communications network via the communications subsystem, the schedule data indicating an identifier of a target medication pack of the set of multiple medication packs and a time at which a medication of the target medication pack is to be dispensed;
identifying a target cabinet enclosure having an identifier that is associated with the identifier of the target medication pack indicated by the schedule data; and
providing an electronic command to the lock assembly to individually unlock the enclosure door of the target cabinet enclosure from an initial locked state at the time indicated by the schedule data.

10. The method of claim 9, further comprising:
at a subsequent time following the time indicated by the schedule data, for at least the target cabinet enclosure:
receiving the identifier of the target medication pack and the data indicating an updated enclosure state of each of the one or more medication enclosures of the target medication pack via the wireless receiver associated with the target cabinet enclosure,
associating the identifier of that target medication pack with the identifier of the target cabinet enclosure within the cabinet-based data storage machine based on the wireless receiver via which the identifier of the target medication pack was received,
upon receiving the identifier of the target medication pack, provide a subsequent electronic command to the lock assembly to individually lock the enclosure door of the target cabinet enclosure from an unlocked state at the subsequent time,
identifying the door state of the enclosure door of the target cabinet enclosure following the subsequent electronic command, and
transmitting updated event data to the remote computing system over the wide-area communications network, the updated event data indicating the identifier of the target medication pack associated with the identifier of the target cabinet enclosure, the updated enclosure state of each of the one or more medication enclosures of the target medication pack, and the door state of the target enclosure door.

11. The method of claim 7, wherein the wireless receiver is a near-field wireless receiver located within the storage region of the cabinet;
wherein the cabinet enclosure defined by an enclosure body and an enclosure door provides electromagnetic shielding; and
wherein the method further comprises:
determining that the medication pack is located within the storage region when the enclosure door is closed based on a wireless signal strength of wireless signals received from the wireless transmitter of the medication pack exceeding a threshold signal strength; and
associating the identifier of the medication pack received via the near-field wireless receiver with the presence identifier if the medication pack is determined to be located within the storage region based on the wireless signal strength.

12. The method of claim 7, wherein the identifier of the medication pack includes RFID.

13. An article, comprising:
a data storage machine having instructions stored thereon executable by a logic machine to:
at a cabinet enclosure of a medical cabinet system defined by an enclosure body and an enclosure door collectively forming a storage region therein:
receive, via a wireless receiver from a wireless transmitter of a medication pack object located within the storage region, an identifier of the medication pack wherein the medication pack has one or more discrete medication enclosures;

associate the identifier of the medication pack received via the wireless receiver with a presence identifier indicating presence of the medication pack within the storage region;

receive, via the wireless receiver from the wireless transmitter of the medication pack located within the storage region, data indicating an enclosure state of each of the one or more discrete medication enclosures of the medication pack;

identify, via a sensor subsystem, a door state of the enclosure door of the cabinet enclosure as being either locked or unlocked, or either opened or closed; and transmit, via a communications subsystem, event data to a remote computing system over a wide-area communications network, the event data indicating the identifier of the medication pack, the door state of the enclosure door, the enclosure state of each of the one or more discrete medication enclosures of the medication pack, and the presence identifier of the medication pack.

14. The article of claim 13, wherein the medical cabinet system further includes:

a storage assembly located within the storage region of the cabinet enclosure that defines a receptacle that accommodates the medication pack that is removable from the receptacle, and a receptacle lock assembly operable to lock the medication pack within the receptacle in which the medication pack is not removable from the receptacle if the receptacle lock assembly is locked and unlock the medication pack in which the medication pack is removable from the receptacle, wherein the sensor subsystem being further operable to detect a receptacle state for the receptacle as being locked or unlocked by the receptacle lock assembly; and wherein the instructions are further executable by the storage machine to transmit the event data to the remote computing system further indicating the receptacle state.

15. The article of claim 13, wherein the medical cabinet system further includes a door lock assembly operable to lock and unlock the enclosure door responsive to an electronic command;

wherein the medication pack is one of a set of multiple medication packs; and wherein the instructions are further executable by the storage machine to:

receive a medication dispensing schedule data over the wide-area communications network via the communications subsystem, the schedule data indicating an identifier of a target medication pack of the set of multiple medication packs and a time at which a medication of the target medication pack is to be dispensed;

identify a target cabinet enclosure having an identifier that is associated with the identifier of the target medication pack indicated by the schedule data; and provide an electronic command to the lock assembly to individually unlock the enclosure door of the target cabinet enclosure from an initial locked state at the time indicated by the schedule data.

16. The article of claim 15, wherein the instructions are further executable by the storage machine to:

at a subsequent time following the time indicated by the schedule data, for at least the target cabinet enclosure:

receive the identifier of the target medication pack and the data indicating an updated enclosure state of each of the one or more medication enclosures of the target medication pack via the wireless receiver associated with the target cabinet enclosure, associate the identifier of that target medication pack with the identifier of the target cabinet enclosure within the cabinet-based data storage machine based on the wireless receiver via which the identifier of the target medication pack was received, upon receiving the identifier of the target medication pack, provide a subsequent electronic command to the lock assembly to individually lock the enclosure door of the target cabinet enclosure from an unlocked state at the subsequent time, identify the door state of the enclosure door of the target cabinet enclosure following the subsequent electronic command, and transmit updated event data to the remote computing system over the wide-area communications network, the updated event data indicating the identifier of the target medication pack associated with the identifier of the target cabinet enclosure, the updated enclosure state of each of the one or more medication enclosures of the target medication pack, and the door state of the target enclosure door.

17. The article of claim 13, wherein the wireless receiver is a near-field wireless receiver located within the storage region of the cabinet;

wherein the cabinet enclosure defined by an enclosure body and an enclosure door provides electromagnetic shielding; and wherein the instructions are further executable by the storage machine to:

determine that the medication pack is located within the storage region when the enclosure door is closed based on a wireless signal strength of wireless signals received from the wireless transmitter of the medication pack exceeding a threshold signal strength; and associate the identifier of the medication pack received via the near-field wireless receiver with the presence identifier if the medication pack is determined to be located within the storage region based on the wireless signal strength.

* * * * *

UNITED STATES PATENT AND TRADEMARK OFFICE
CERTIFICATE OF CORRECTION

PATENT NO. : 11,617,436 B1
APPLICATION NO. : 16/827131
DATED : April 4, 2023
INVENTOR(S) : Dennis Michael McNannay and Dewey Nigma, Jr.

Page 1 of 1

It is certified that error appears in the above-identified patent and that said Letters Patent is hereby corrected as shown below:

In the Claims

In Column 22, Claim 13, Line 67, delete "object".

Signed and Sealed this
Twenty-third Day of May, 2023

Katherine Kelly Vidal
*Director of the United States Patent and Trademark Office*